United States Patent

Müller et al.

[11] 4,051,204
[45] Sept. 27, 1977

[54] APPARATUS FOR MIXING A LIQUID PHASE AND A GASEOUS PHASE

[75] Inventors: Hans Müller, Zurich; Konstantin Sotirianos, Stafa, both of Switzerland

[73] Assignee: Hans Müller, Mannedorf, Switzerland

[21] Appl. No.: 694,943

[22] Filed: June 11, 1976

Related U.S. Application Data

[63] Continuation of Ser. No. 534,898, Dec. 20, 1974, abandoned.

[30] Foreign Application Priority Data

Dec. 21, 1973  Switzerland ............... 18125/73
Dec. 21, 1973  Switzerland ............... 18126/73

[51] Int. Cl.² ............................................. B01F 3/04
[52] U.S. Cl. .................................... 261/36 R; 195/142; 195/143; 366/101; 366/164; 261/93; 261/123; 261/124; 261/DIG. 75
[58] Field of Search ................. 261/36 R, 77, 87, 93, 261/123, DIG. 75, 29, 124; 209/169; 195/109, 142–144; 259/23; 239/143, 550, 561

[56] References Cited

U.S. PATENT DOCUMENTS

| 2,244,902 | 6/1941 | Stich .................... 261/93 X |
| 2,246,560 | 6/1941 | Weinig et al. ............... 261/93 |
| 2,772,863 | 12/1956 | Harney et al. ............. 261/93 X |
| 2,780,490 | 2/1957 | Sigvardt .................. 239/561 X |
| 3,393,802 | 7/1968 | Logue et al. ............... 261/93 X |
| 3,625,834 | 12/1971 | Muller .................... 261/93 X |
| 3,650,950 | 3/1972 | White .................... 261/87 X |
| 3,776,531 | 12/1973 | Ebner et al. ............... 261/87 |
| 3,820,759 | 6/1974 | Hege ..................... 261/87 X |
| 3,827,679 | 8/1974 | Kaelin ................... 261/93 X |
| 3,846,516 | 11/1974 | Carlson .................. 261/87 |

FOREIGN PATENT DOCUMENTS

| 48,730 | 4/1934 | Denmark ................. 261/93 |
| 1,474,582 | 3/1967 | France ................... 261/87 |
| 2,042,791 | 3/1971 | Germany ................. 261/93 |
| 562,894 | 7/1944 | United Kingdom .......... 261/93 |
| 548,664 | 10/1942 | United Kingdom .......... 261/93 |

*Primary Examiner*—Tim R. Miles
*Assistant Examiner*—Richard L. Chiesa
*Attorney, Agent, or Firm*—Michael J. Striker

[57] ABSTRACT

A vessel is adapted to contain a liquid phase and a tubular guide baffle in the vessel has spaced open ends one of which at least in part bounds a venturi-shaped passage. A rotary impeller in the vessel has an axial inlet communicating with the one open end and a plurality of peripheral outlets which communicate with the axial inlet. A drive is provided for rotating the impeller so that centrifugal action causes expulsion of liquid phase from the outlets and thereby creates suction in the venturi-shaped passage to draw additional liquid phase from the guide baffle into the inlet. Gas admitting arrangements are provided, including a plurality of nipples communicating with the passage and with a conduit through which gas is supplied, so that the suction in the venturi-shaped passage draws gas from the source via the conduit and the nipples and the gas becomes admixed with the liquid phase.

5 Claims, 2 Drawing Figures

APPARATUS FOR MIXING A LIQUID PHASE AND A GASEOUS PHASE

CROSS-REFERENCE TO RELATED APPLICATION

This is a continuation of application Ser. No. 534,898, filed on Dec. 20, 1974, now abandoned.

BACKGROUND OF THE INVENTION

The present invention relates generally to an apparatus for mixing a liquid phase and a gaseous phase, and more particulaly to an apparatus of this type wherein no pressurized source of the gaseous phase is required.

There are instances in which a gaseous phase must be mixed with a liquid phase, for example to aerate the liquid phase, as is required in the aerobic growing of microorganism such as yeast, fungi and bacteria.

In most of the prior-art apparatus for this purpose the gaseous phase is admitted into the vessel containing the liquid phase, from a source of such gaseous phase under compression, for example from a blower or the like. This requires extra energy to operate the blower or the like and makes the equipment not only more expensive to produce but also more expensive to operate.

An attempt has therefore been made in the prior art to provide an apparatus of this type in which suction develops within the vessel accommodating the liquid phase, in order to thereby aspirate the gaseous phase without requiring that the gaseous phase be in pressurized condition. This has represented a step forward over the art preceding that last proposal, but experience has shown that in many instances the pressure head than can be obtained is not sufficient, so that the amount of gaseous phase that can be aspirated is inadequate to obtain optimum growth conditions for the microorganisms or the like.

SUMMARY OF THE INVENTION

Accordingly, it is a general object of this invention to overcome the disadvantages of the prior art.

More particularly, it is an object of the present invention to provide an improved apparatus for mixing a liquid phase or a gaseous phase, which is not possessed of the disadvantages of the prior art.

In keeping with these objects, and with others which will become clear hereafter, the invention resides in an apparatus for mixing a liquid phase and a gaseous phase which, according to one aspect of the invention, comprises a vessel adapted to contain a liquid phase, and a tubular guide baffle in the vessel and having spaced open ends one of which at least in part bounds a venturi-shaped passage. A rotary impeller is located in the vessel and has an axial inlet communicating with the one open end of the tubular baffle, and a plurality of baffle outlets which communicate with the axial inlet. Drive means is provided for rotating the impeller so that centrifugal action causes expulsion of liquid phase from the outlets and creates suction in the venturi-shaped passage to thereby draw additional liquid phase from the guide baffle into the inlet. Gas-admitting means is provided, comprising a plurality of nipples which communicate with the passage, and a conduit communicating wit the nipples and with a source of gas so that the suction in the passage draws gas from the source via the conduit and the nipples.

It will be understood that the gaseous phase may of course be air or a different gas, as will be dictated by the particular requirements of a specific application.

The nipples may be of identical or different length, they may be of identical or different diameter, they may be inclined axially of the inlet in the direction away from the baffle and/or the ends of the nipples which are located in the venturi-shaped passage may be cut off at an angle to the elongation of the nipples, so as to be slanted axially of the passage.

The nipples are advantageously distributed not only circumferentially of the passage but also at different levels transversely of the axial elongation of the venturi-shaped passage.

If these nipples are of different lengths, this assures that air or other gaseous phase is aspirated by suction everywhere into the liquid phase flowing through the passage, that is air or other gaseous phase is aspirated into the flowing liquid over the entire cross section thereof as it passes through the passage. This results, inter alia, in a substantially better suction which in turn produces a substantially improved aspiration of quantities of gaseous phase, so that a predispersing of the gaseous phase and the liquid phase takes place before the phase even leave the impeller to enter into the vessel. This in turn results, if air is being aspirated, in an improved supply of oxygen to the microorganisms to be aerated.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
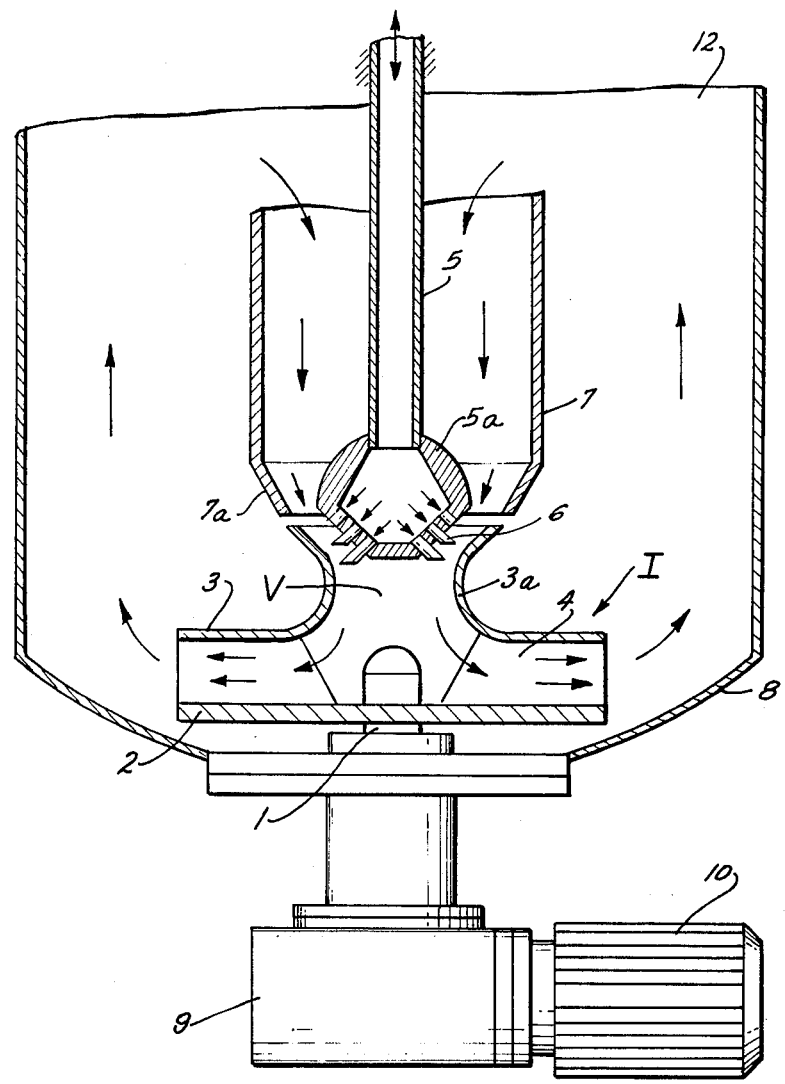
FIG. 1 is an axial section through an embodiment of the invention.

Referring now firstly to the embodiment in FIG. 1 it wll be seen that reference numeral 1 identifies a drive shaft on which an impeller I is mounted. The impeller I is essentially composed of a plate or disc 2 upwardly of which there is provided a further plate or disc 3 spaced from the plate 2; the plates 2 and 3 are connected with one another by a plurality of radially extending guide vanes 4 which extend between the plates 2 and 3 and from the center region outwardly towards the periphery of the impeller I. The impeller I is rotated when the shaft 1 is rotated.

The impeller I is mounted in a vessel 12 the upper end of which is not shown and in which there is also located a guide baffle 7 beneath the lower end of which the impeller I is locatedd. Extending axially through the guide baffle 7 is an air supply conduit 5 the lower end of which is identified with reference numeral 5a and of enlarged configuration. The end portion 5a, together with the lower end portion 7a of the guide baffle 7 and with a central hub portion 3a of the plate 3 form a constricted venturi-shaped passage V through which liquid phase is drawn through the baffle 7 axially when the impeller I rotates and expels liquid phase between the circumferentially spaced radially extending guide vanes 4, at the periphery of the impeller. This expulsion causes suction in the passage V and results in additional liquid being drawn into the passage via the guide baffle 7. The portion 5a is provided with a plurality of small nipples 6 communicating with its interior and also communicating with the passage V. These nipples are of different length but may also be of the same length, and they are slanted downwardly into the inlet of the hub portion 3a. They are also located in different planes as seen with respect to the transverse direction of the passage V.

The suction which develops in the passage V, when the impeller I is rotated as rotation is transmitted to the shaft 1 via the drive 9 that is powered by an electromotor 10, aspirates air or whatever gaseous phase is avialable to the conduit 5 from an appropriate source, such as the ambient atmosphere, and this air becomes discharged into the liquid phase flowing through the Venturi passage V so as to become dispersed therein. The more of the nipples 6 are present, the more intensive will be the mixing of the gaseous and liquid phases. The different lengths of the nipples 6, if that is indeed what is chosen as in FIG. 1, assures that substantially the entire cross-sectional area of the passage V will have gaseous phase discharged into it so that in addition to a large quantity of gaseous phase per unit time there will also be a bounce effect obtained for the flowing liquid with respect to the outer walls of the nipples 6, causing eddy currents which further improve the mixing of the gaseous and liquid phases. It is advantageous if the conduit 5 is so mounted that it can be raised and lowered, as diagrammatically illustrated, so that the individual nipples 6 can thereby also be raised and lowered within the passage V.

Figure 2:
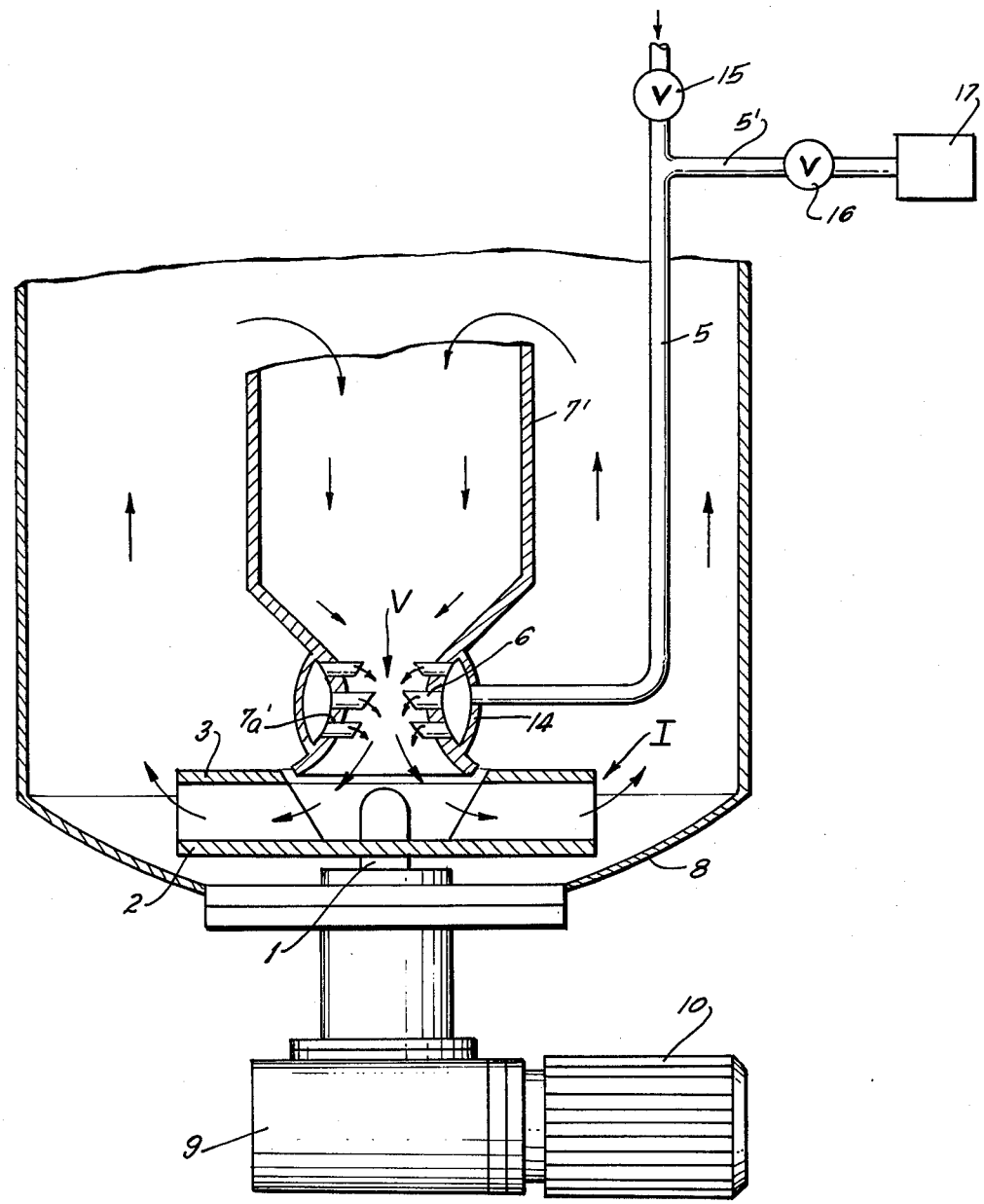
FIG. 2 is a view analogous to FIG. 1 but showing a different embodiment.

FIG. 2 shows an analogous embodiment wherein like reference numerals identify like components. In this embodiment the lower end 7a' of the guide baffle 7' is strongly constricted in the direction towards the impeller I to form the Venturi-shaped passage V. A plurality of nipples 6 are mounted in the end portion 7a' and extend at different transverse levels into the passage V. The outer ends of the nipples 6 extend into an annular conduit 14 that surrounds the end portion 7a' and which is in communication with the gaseous-phase supply conduit 5, for instance a conduit which communicates with the ambient atmosphere.

The drive is again by means of a drive unit 9 which is located outside the vessel wall 8 and which is powered by an electric motor 10. When the drive is energized, liquid phase is drawn via the impeller I through the guide baffle 7' the upper end of which is open and communicates with the interior of the vessel. As it travels through the venturi passage V, the liquid is so strongly accelerated that it creates suction in the passage V, which suction aspirates gaseous phase via the nipples 6, the conduit 14 and the conduit 5, so that the gaseous phase is aspirated without requiring a blower, compressor or a source of compressed gaseous phase. If the ends of the nipples 6 are downwardly bevelled as illustrated, and/or if the nipples 6 are themselves downwardly inclined as shown in FIG. 1, the effect is even more pronounced. The more nipples 6 are located at different levels, the stronger will be the mixing of the gaseous phase with the liquid phase. The thus-obtained dispersion now flows through the impeller and is therein once more accelerated as it is centrifugally ejected from the periphery of the impeller. This is a pre-dispersion which is then followed by a further intensive mixing of the gaseous phase with the liquid phase in the vessel, by appropriate paddles or other devices which are not shown because they do not form a part of the invention.

The cumulative effects obtained by the present invention assure that excellent aeration or otherwise admixing of a gaseous phase with a liquid phase is obtained, which is highly important for maximum growth of many microorganisms.

Of course, not the least of the advantages of the present invention is the fact that no compressors, blowers or other sources are required to produce compressed gaseous phase. It should be understood, however, that if it is desired compressed gaseous phase can be in addition or alternately submitted via the conduit 5 for example, as has been diagrammatically shown in FIG. 2 where a branch conduit 5' communicates with the conduit 5 and where two valves 15 and 16 are interposed in the conduits 5 and 5'. The latter leads to a diagrammatically illustrated source 17 of compressed gaseous phase, for example compressed air. If only phase from the source 17 is to be admitted, then the valve 15 will be closed and the valve 16 opened; if only gaseous phase via the conduit 5 is to be admitted, then the valve 16 will be closed and the valve 15 opened, or both types of gaseous phase can be admitted simultaneously (they need not necessarily be identical) in which case the valves 15 and 16 are simultaneously opened.

It will be understood that each of the elements described above, or two or more together, may also find a useful application in other types of constructions differing from the types described above.

While the invention has been illustrated and described as embodied in an apparatus for mixing liquid and gaseous phase, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In an apparatus for mixing a liquid phase and a gaseous phase, particularly a fermentor for biologically growing microorganisms, a combination comprising a vessel adapted to contain a liquid phase; a tubular guide baffle in said vessel and having spaced open ends one of which at least in part bounds a venturi-shaped passage having a throat portion; a rotary impeller mounted in said vessel for rotation about an axis and having an axial inlet communicating with said open end, and a plurality of peripheral outlets which communicate with said axial inlet; drive means for rotating said impeller about said axis so that centrifugal action causes expulsion of liquid phase from said outlets and creates suction in said venturi-shaped passage to thereby draw additional liquid phase from said guide baffle into said inlet; and gas admitting means including a conduit which communicates with a source of gaseous phase, and a plurality of tubular nipples each having an elongated tubular end portion which extends into said throat portion in direction generally transverse to the axial flow of liquid phase, each tubular end portion terminating in a bevelled discharge port which is inclined at a substantially constant angle of inclination relative to the elongation of the respective tubular end portion and which faces generally downstream of the axial flow of liquid phase, said discharge ports communicating with different locations of said passage so that the suction in said throat portion of said passage draws said gaseous phase from said source via said conduit and ejects said gaseous phase out of said discharge ports of said nipples across different transverse sections of said throat portion without requiring said gaseous phase to be in pressurized condition.

2. A combination as defined in claim 1, wherein each tubular nipple is inclined at an angle of inclination relative to said axis of rotation; and wherein each discharge port is inclined substantially normally of said axis, said discharge ports lying in a plurality of substantially parallel planes.

3. A combination as defined in claim 1, wherein said tubular nipples extend substantially normally of said axis in a plurality of planes which are substantially parallel relative to each other; and wherein each discharge port is inclined at an angle of inclination relative to said axis of rotation.

4. In an apparatus for mixing a liquid phase and a gaseous phase, particularly a fermentor for biologically growing microorganisms, a combination comprising a vessel having an interior adapted to contain a liquid phase; a hollow tubular guide baffle in said vessel, said baffle having one open end region which communicates with the interior of said vessel and another spaced open end region which converges in direction away from said one open end; a rotary impeller mounted in said vessel for rotation about an axis, said impeller having an axial inlet which communicates with said other open end region of said baffle, a plurality of peripheral outlets which communicate with the interior of said vessel, and a venturi-shaped passage intermediate said inlet and said outlets, said venturi-shaped passage having an upstream converging portion, a downstream diverging portion, and a throat portion intermediate said upstream and downstream portions; drive means for rotating said impeller about said axis and for expelling liquid phase from said outlets by centrifugal action, said drive means generating a suction force in said venturi-shaped passage which is operative for drawing additional liquid phase in a path from the interior of said vessel through said hollow baffle towards said axial inlet and from there through said venturi-shaped passage towards said outlets for expulsion from the latter into the interior of said vessel; and gas-admitting means including a hollow supply conduit mounted coaxially in said hollow baffle and communicating with a source of gaseous phase, and also including a plurality of tubular nipples mounted on and communicating with said supply conduit, said tubular nipples having elongated tubular end portions which extend into said venturi-shaped passage in direction transversely of said path and which are inclined at an angle of inclination relative to said axis of rotation, each tubular end portion terminating in a beveled discharge port which is inclined at a substantially constant slope relative to the elongation of the respective tubular end portion and which lies in a plane that extends substantially normally of said axis, each discharge port facing downstream of said path and communicating with a different location of said venturi-shaped passage and at a different portion of said path so that the suction force generated in said venturi-shaped passage draws the gaseous phase from the source through said supply conduit towards said nipples and from there through said tubular end portions towards said discharge ports for discharge across different transverse sections of said venturi-shaped passage for mixing with the liquid phase flowing through the latter without requiring the gaseous phase to be in pressurized condition.

5. In an apparatus for mixing a liquid phase and a gaseous phase, particularly a fermentor for biologically growing micro-organisms, a combination comprising a vessel having an interior adapted to contain a liquid phase; a hollow tubular drive baffle in said vessel, said baffle having one open end region which communicates with the interior of said vessel and another venturi-shaped open end region, said other venturi-shaped end region having an upstream converging portion, a downstream diverging portion, and a throat portion intermediate said upstream and downstream portions; a rotary impeller mounted in said vessel for rotation about an axis, said impeller having an axial inlet which communicates with said downstream diverging portion of said other venturi-shaped end region, and a plurality of peripheral outlets which communicate with the interior of said vessel; drive means for rotating said impeller about said axis and for expelling liquid phase from said outlet by centrifugal action, said drive means generating a suction force in said other venturi-shaped end region which is operative for drawing additional liquid phase in path through said one open end region and from there through said other venturi-shaped end region towards said axial inlet to be expelled from said outlet into the interior of said vessel; and gas-admitting means including a hollow annular supply conduit surrounding said throat portion on said baffle and communicating with a source of gaseous phase, and also including a plurality of tubular nipples mounted on said other venturi-shaped end region of said baffle and communicating with said annular supply conduit, said tubular nipples having elongated tubular end portions which extend into said other venturi-shaped end region in direction transversely of said path and substantially normally of said axis, each tubular end portion terminating in a bevelled discharge port which is inclined at a substantially constant angle of inclination relative to the elongation of the respective tubular end portion, each discharge port facing generally downstream of said path and communicating with a different location of said other venturi-shaped end region and at a different portion of said path so that the suction force generated in said other venturi-shaped end region draws the gaseous phase from the source through said annular supply conduit towards said nipples and from there through said tubular end portions toward said discharge ports for discharge across different transverse sections of said other venturi-shaped end region for mixing with the liquid phase flowing through the latter without requiring the gaseous phase to be in pressurized condition.

* * * * *